United States Patent [19]
Katner et al.

[11] 4,087,429
[45] May 2, 1978

[54] 5' ACETOXY VINBLASTINE 4' BIS-SULFITE

[75] Inventors: Allen S. Katner; Gerald E. Gutowski; Jean C. Miller, all of Indianapolis, Ind.

[73] Assignee: Eli Lilly and Company, Indianapolis, Ind.

[21] Appl. No.: 734,151

[22] Filed: Oct. 20, 1976

[51] Int. Cl.² ........................................... C07D 519/04
[52] U.S. Cl. ................................. 260/287 B; 424/258
[58] Field of Search ..................................... 260/287 B Primary Examiner—Donald G. Daus
Assistant Examiner—David E. Wheeler
Attorney, Agent, or Firm—James L. Rowe; Everet F. Smith

[57] ABSTRACT

Vincaleukoblastine (VLB, vinblastine) is reacted with thionyl chloride to form a bis-sulfite ester which is converted to various 5'-oxygenated derivatives.

1 Claim, No Drawings

5' ACETOXY VINBLASTINE 4' BIS-SULFITE

BACKGROUND OF THE INVENTION

Vincoleukoblastine (VLB, vinblastine) was the first of the dimeric indole alkaloids to be used in the treatment of malignancies. The compound is the subject of U.S. Pat. No. 3,097,137, to Beer, Cutts and Noble. The next of the dimeric indole alkaloids to be used in the treatment of malignancies, and in particular of the acute leukemias of childhood, was leurocristine (vincristine)—see U.S. Pat. No. 3,205,220 to Svoboda, Barnes and Armstrong. Also claimed in this latter patent was the dimeric vinca alkaloid, leurosidine, an isomer of VLB. VLB, vincristine, and leurosidine can all be represented by Formula I below as follows:

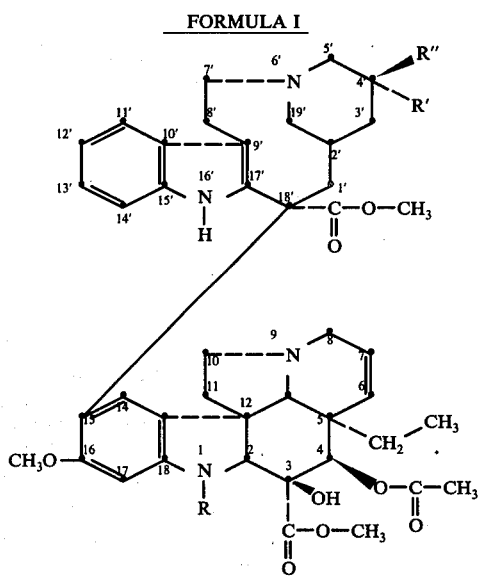

FORMULA I

In Formula I, when R is formyl, R' is ethyl, and R" is hydroxy, the resulting compound is vincristine; when R is methyl, R' is ethyl, and R" is hydroxy, the compound is VLB. Leurosidine, being a C-4' epimer of vinblastine, is represented by Formula I when R is methyl, R' is hydroxy, and R" is ehtyl. Originally, leurosidine was thought to have a structure isomeric (rather than epimeric) with VLB in that the hydroxyl group was believed to be at 3' rather than 4'—see Neuss, Huckstep, and Cone, *Tetrahedron Letters*, 811, (1967). More recently, however, Wenkert et al. publishing in *Helvetica Chimica Acta*, 58, 1560 (1975) have shown that leurosidine is not the 3'-hydroxy isomer of VLB but is the 4' epimer having an α-hydroxyl and a β-ethyl group.

Recently, we have invented a process for converting VLB to leurosidine by forming a 4'-bis-sulfite ester of VLB and then reacting this ester with silver perchlorate to form VLB perchlorate. This process is disclosed in our copending application Ser. No. 687,274, filed Jan. 17, 1976.

Functional derivatives of VLB, vincristine or leurosidine at 5' are not known.

SUMMARY OF THE INVENTION

This invention provides 5'-oxygenated derivatives of VLB 4'-bis-sulfite ester. These derivatives can be represented by the following structure:

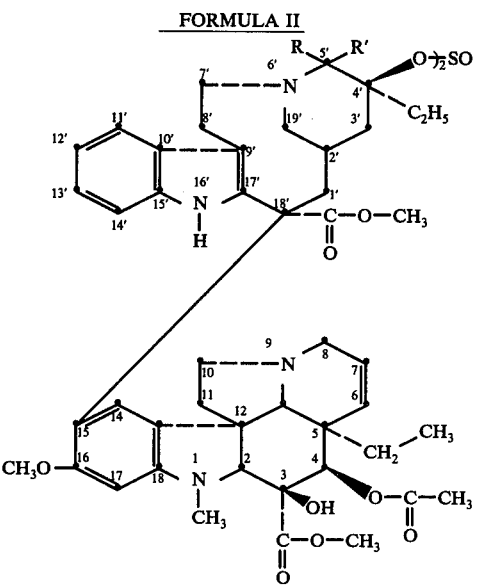

FORMULA II wherein one of R and R', when taken singly, is H and the other is OH, O-mesyl, OAc or OPr and, when taken together with the carbon to which they are attached, form a carbonyl group.

The bis-sulfite ester (Formula II wherein both R and R' are H) is prepared by the action of thionyl chloride on VLB in the presence of pyridine.

Treatment of this bis-sulfite ester with silver perchlorate in an aqueous solvent yields as a predominant product leurosidine as the perchlorate salt and as a minor product 5'-hydroxy VLB 4-bis-sulfite ester (II above when one of R and R' is OH). Treatment of the same bis-sulfite ester with silver acetate or silver propionate yields 5' acetoxy VLB bis-sulfite ester (Formula II wherein one of R and R' is H and the other is OAc or OPr). Alternatively, treatment of the 5'-hydroxy derivative with acetic or propionic anhydride or with methanesulfonyl chloride in the presence of pyridine yields compounds according to II wherein one of R and R' is H and the other is OAc, OPr or O-mesyl.

Compounds in which R and R' plus the carbon to which they are attached form a carbonyl are prepared by oxidizing 5'-hydroxy VLB 4'-bis-sulfite ester, as with N-chloro succinimide.

The preparation of the bis-sulfite ester, the starting material used for a preparation of certain of the compounds of this invention, involves the use of a large excess of thionyl chloride, for example a 10-20 fold excess. The solvent of choice for this reaction is pyridine although other aromatic tertiary amine bases such as α-picoline can be used. In the second step of the reaction sequence; i.e., the oxidation of the bis-sulfite ester at C-5' (along with the formation of leurosidine perchlorate) silver perchlorate in a slight excess (10 percent) is employed in an aqueous solvent system. The preferred solvent is a mixture of water and tetrahydrofuran (THF). Other water-miscible solvents which do not react with silver perchlorate such as dioxane can be used in place of THF in the above hydrolytic system.

The invention is further illustrated by the following specific examples:

EXAMPLE 1

Preparation of VLB 4'-Bisulfite Ester

A solution of 62 g. of VLB was prepared in 700 ml. of anhydrous pyridine. The solution was cooled to a temperature in the range of −15° to −8° C. 19 ml. of thionyl chloride previously purified by distillation from sulfur were added in dropwise fashion over a 15 minute period while the temperature was maintained in the above range. The reaction mixture was stirred in the same temperature range for an additional 2 hours and was then quenched in about 5 liters of an ice-water mixture. The reaction product comprising VLB 4'-bis-sulfite ester was collected by filtration and chromatographed over 600 g. of florisil, employing an ethylacetate-chloroform solvent mixture as the eluting agent. Fractions shown to contain bis-sulfite ester were combined and the solvent evaporated therefrom in vacuo. The resulting residue was recrystallized from a methylene dichloride-methanol solvent mixture to yield about 10 g. of VLB 4'-bis-sulfite.

EXAMPLE 2

Preparation of 5'-Hydroxy VLB 4'-Bis-Sulfite Ester

A suspension of 2.0 g. of VLB 4'-bis-sulfite ester in 100 ml. of THF was prepared. A solution of 560 mg. of silver perchlorate dissolved in 25 ml. of water was added thereto. After stirring the resulting mixture for about 4.5 hours, thin-layer chromatography showed that the starting bis-sulfite ester had been entirely converted into equal quantities of leurosidine and of 5'-hydroxy VLB bis-sulfite ester. Volatile constituents were removed from the reaction mixture in vacuo and the aqueous solution remaining was partitioned with ethyl acetate. Filtration of the two layers yielded about 980 mg. of a white solid comprising leurosidine perchlorate, a high melting, water-insoluble white solid.

The aqueous filtrate was subjected to a further two-fold extraction with ethyl acetate. The ethyl acetate layers were separated and combined and the solvent removed by evaporation. Recrystallization from ethyl acetate of the resulting residue yielded 746 mg. of 5'-hydroxy-VLB 4'-bis-sulfite ester; MP = 230° C (with decomposition).

EXAMPLE 3

Preparation of 5'-Keto VLB 4'-Bis-Sulfite Ester

A solution was prepared from 67 mg. of N-chlorosuccinimide in 1.5 ml. of toluene. The solution was cooled to about 0° C. while 31 mg. of dimethyl sulfide were added with stirring. A white precipitate resulted. Next, a solution of about 50 mg. of 5'-hydroxy VLB 4'-bis-sulfite ester in about 1.5 ml. of a 1:1 toluene:methylene dichloride solvent was added. The reaction mixture was stirred in the cold and then allowed to warm to room temperature over a 2-hour period. Next, 51 mg. of triethylamine were added. The stirring of the reaction mixture was continued for an additional 15 minutes after which time it was filtered. Evaporation of the filtrate to dryness left a residue comprising 5'-keto VLB 4'-bis-sulfite ester, which residue was partitioned between chloroform and water. The chloroform extract containing the 5'-keto bis-sulfite ester was separated and the chloroform evaporated therefrom. Mass spectrographic analysis indicated an apparent molecular ion peak at 806 for the oxidation product, 5'-keto VLB 4'-bis-sulfite ester. The starting material, the 5'-hydroxy compound, had an apparent molecular ion at 808. The actual molecular weight of the 5'-hydroxy VLB 4'-bis-sulfite ester is 1698. Because of the thermal instability of the ester in the mass spectrometer, an "apparent molecular ion" of 808 is actually observed, caused by the loss of the elements of $H_2SO_3$ from the tetrameric (2 indole and 2 dihydro indole moieties) molecule and results in what are probably two identical dimeric Vinca fragments with the molecular weight of 808 as observed. The elemental composition of the bisulfite ester was confirmed by elemental analysis, as well as by an osmometric molecular weight determination, thus verifying its tetrameric nature. Upon oxidation as described above, the resultant 5'-keto VLB 4'-bis-sulfite ester (actual molecular weight 1696), exhibits an anologous breakdown in the mass spectrometer to produce a highest observed mass peak at 806. VLB 4'-bis-sulfite ester itself also displays this type of behavior in the mass spectrometer with the observed highest mass ion being formed at 792, instead of at 1666, actual molecular weight of this tetrameric alkaloid. Again in this case, osmometric molecular weight determinations and elemental analysis confirm the conclusion as to the nature of the product. This proposed thermally induced loss of $H_2SO_3$ in the mass spectrometer is a well documented mode of breakdown of sulfite esters. NMR confirmed the expected structure.

EXAMPLE 4

Preparation of 5'-Acetoxy VLB 4'-Bis-Sulfite Ester

A solution was prepared containing 103.2 mg. of 5'-hydroxy VLB 4'-bis-sulfite ester in 10 ml. of pyridine. The solution was cooled to a temperature in the range 0.5° C. A solution of 0.2 ml. of acetic anhydride in 5 ml. of pyridine was added thereto. The reaction mixture was stirred for about 2 hours. The volatile constituents were removed by evaporation in vacuo, and the resulting residue dissolved in methanol. The methanolic solution was allowed to stand for about 15 minutes, the methanol was then removed by evaporation in vacuo. This procedure was repeated. The residue was then dissolved in water containing a few drops on 1N aqueous hydrochloric acid. The acidic solution was made basic with 10 percent ammonium hydroxide, and the resulting basic solution extracted three times with methylene dichloride. The methylene dichloride extracts were combined, dried, and the solvent removed by evaporation. Thin-layer chromatography indicated that the resulting residue was a mixture of 5'-acetoxy VLB 4'bis-sulfite ester and 3,5'-diacetoxy VLB 4'-bis-sulfite ester. The two products were separated by thick layer chromatography over silica. 24.3 mg. of 5'-acetoxy VLB 4'-bis-sulfite ester were obtained. Molecular spectrum peaks at (852) 806, 747, 647, 538–40, 282, 144, 135. NMR δ = 0.84, 0.102 (shifted), 2.10 2.20 (new acetate), 2.76, 3.58, 3.80, 4.80 (double bump shifted). The 3-acetoxy group of 3,5'-diacetoxy VLB 4'-bis-sulfite ester can be reconverted to a 3-hydroxy group by the procedure of Hargrove, *Lloydia*, 27, 340 (1964) to yield further 5'acetoxy VLB 4'-bis-sulfite ester.

The corresponding propionoxy derivative can be prepared by substituting propionic anhydride in the above reaction.

Following the above procedure, 5'-hydroxy VLB 4'-bis-sulfite ester was reacted with methylsulfonyl chloride in pyridine. The reaction was carried out and the products isolated as above. A mixture of products comprising 5'-mesyloxy VLB 4'-bis-sulfite ester and the corresponding 3,5'-dimesyloxy derivatives were separated by thick-layer chromatography. 5'-mesyloxy VLB αb'-bis-sulfite ester had the following physical characteristics: NMR δ = 0.83, 1.04, 2.73, 3.28 (5'-OSC$\underline{H}_3$), 3.58, 3.80, 4.26. Infrared spectrum: new peaks at 1132 and 1325 cm$^{-1}$.

The compounds of this invention are useful as general CNS depressants having sedative action. 5'-Acetoxy VLB 4'-bis-sulfite ester is also an anti-mitotic agent, and causes metaphase arrest in Chinese hamster ovary cells (See *Cancer Research*, 26, 2131 (1966) for a description of this experimental technique) at a concentration of 0.2 mcg./ml. In addition, certain of the compounds are useful as intermediates; for example, 5'-hydroxy VLB 4'-bis-sulfite ester can be reacted with acetic anhydride, propionic anhydride methanesulfonyl chloride, etc. to produce the corresponding 5'-acetoxy, 5'-propionoxy, or 5'-mesyloxy derivatives. The compound can be employed as general sedatives in accordance with the procedure employed for the use of sedative drugs.

We claim:

1. 5'-Acetoxy VLB 4'-bis-sulfite ester of the formula

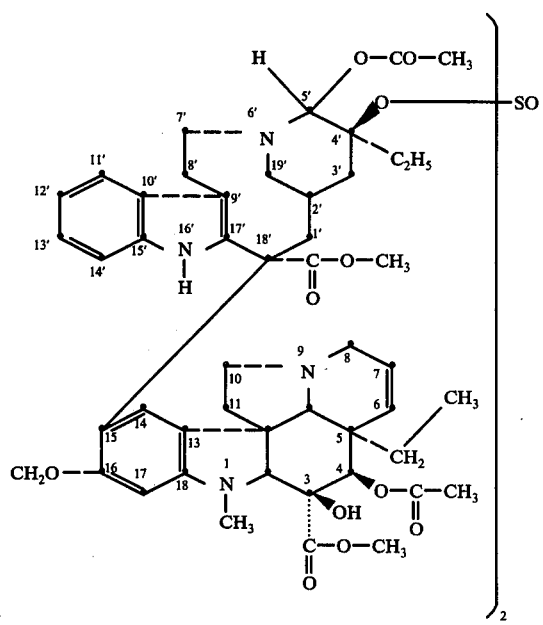

* * * * *